(12) United States Patent
Prestegard

(10) Patent No.: US 8,575,932 B2
(45) Date of Patent: Nov. 5, 2013

(54) UPPER STACK FOR A NUCLEAR MAGNETIC RESONANCE SPECTROMETER A APARATUS AND ASSOCIATED METHOD OF OPERATING A NUCLEAR MAGNETIC RESONANCE SPECTROMETER APPARATUS

(75) Inventor: James H. Prestegard, Watkinsville, GA (US)

(73) Assignee: The University of Georgia Research Foundation, Inc., Athens, GA (US)

(*) Notice: Subject to any disclaimer, the term of this patent is extended or adjusted under 35 U.S.C. 154(b) by 577 days.

(21) Appl. No.: 12/735,241

(22) PCT Filed: Jan. 7, 2009

(86) PCT No.: PCT/US2009/000074
§ 371 (c)(1),
(2), (4) Date: Jun. 24, 2010

(87) PCT Pub. No.: WO2009/103381
PCT Pub. Date: Aug. 27, 2009

(65) Prior Publication Data
US 2012/0007599 A1 Jan. 12, 2012

Related U.S. Application Data

(60) Provisional application No. 61/010,312, filed on Jan. 8, 2008.

(30) Foreign Application Priority Data

Feb. 22, 2008 (DE) .......................... 10 2008 010 687

(51) Int. Cl.
*G01V 3/00* (2006.01)

(52) U.S. Cl.
USPC ........................................................ 324/309

(58) Field of Classification Search
USPC ................................................... 324/300–322
See application file for complete search history.

(56) References Cited

U.S. PATENT DOCUMENTS

| 4,654,592 A * | 3/1987 | Zens .............................. 324/307 |
| 5,814,992 A | 9/1998 | Busse-Grawitz et al. |
| 7,075,303 B2 * | 7/2006 | Cavaluzzi et al. ............ 324/321 |

(Continued)

FOREIGN PATENT DOCUMENTS

JP 2005-093464 1/2005

OTHER PUBLICATIONS

Nagai, H. et al., Development and testing and superfluid cooled 900 MHz NMR magnet, Cryogenics, Sep. 2001, vol. 41, Issued 9, pp. 623-630.

(Continued)

*Primary Examiner* — Dixomara Vargas
(74) *Attorney, Agent, or Firm* — R. Neil Sudol; Coleman Sudol Sapone, P.C.

(57) ABSTRACT

An upper stack for a nuclear magnetic resonance spectrometer apparatus includes a cryostat having one or more chambers for holding samples in a frozen state. A sample loading tube that also allows He delivery extends to the cryostat, and a sample changer mechanism is disposable at least in part proximate to the cryostat for moving specimens from the cryostat to an NMR probe where they can be heated and melted using inductive heating. A sample ejection tube extends from the sample changer mechanism allowing a clear path for heating a sample in an NMR probe using a laser beam.

18 Claims, 4 Drawing Sheets

(56) References Cited

U.S. PATENT DOCUMENTS

| | | | |
|---|---|---|---|
| 7,102,354 B2* | 9/2006 | Ardenkjaer-Larsen et al. | 324/321 |
| 7,187,175 B2* | 3/2007 | Wakuda et al. | 324/319 |
| 7,205,764 B1 | 4/2007 | Anderson et al. | |
| 7,372,274 B2* | 5/2008 | Ardenkjaer-Larsen et al. | 324/321 |
| 7,474,099 B2 | 1/2009 | Boessel et al. | |
| 7,631,507 B2* | 12/2009 | Stautner | 62/51.1 |
| 7,701,218 B2* | 4/2010 | Noonan et al. | 324/319 |
| 7,764,064 B2* | 7/2010 | Reiss et al. | 324/318 |
| 8,154,292 B2* | 4/2012 | Bovier et al. | 324/318 |

OTHER PUBLICATIONS

Goto, A., et al., Development of a dynamic nuclear polarization system based on the optical pumping method, J. of Magnetism & Magnetic Material, Mar. 2007, vol. 310, Iss 2, 2716-2718.

* cited by examiner

UPPER STACK FOR A NUCLEAR MAGNETIC RESONANCE SPECTROMETER AAPARATUS AND ASSOCIATED METHOD OF OPERATING A NUCLEAR MAGNETIC RESONANCE SPECTROMETER APPARATUS

CROSS-REFERENCE TO RELATED APPLICATIONS

This application is the national phase of International Application No. PCT/US2009/000074 filed 7 Jan. 2009 and claims the benefit under 35 U.S.C. §119(e) of U.S. Provisional Patent Application No. 61/010,312 filed 8 Jan. 2008.

BACKGROUND OF THE INVENTION

This invention relates to nuclear magnetic resonance spectrometers. More particularly, this invention relates to the upper stack of a nuclear magnetic resonance spectrometer. This invention also relates to a method for operating a nuclear magnetic resonance spectrometer apparatus.

NMR has many advantages, including its universal applicability as a non-destructive tool for analysis of compounds containing suitable magnetic nuclei, the near quantitative relationship between resonance intensity and molecular abundance, and the sensitivity of NMR observables to molecular structure. NMR suffers severely, however, from limited sensitivity.

A number of methods have been introduced over the years for enhancement of NMR sensitivity in selected applications. These include CIDNP (chemically induced dynamic nuclear polarization), polarization through reaction with para hydrogen, optically detected NMR, transfer from optically pumped Xe or He, and microwave induced DNP (dynamic nuclear polarization). DNP has recently developed to the point of commercialization. It relies on transfer of polarization from electron spins to nuclear spins using either three spin solid-state mechanisms or thermal mixing. The polarization for electrons is a factor of 650 larger than for protons and a factor of 2600 larger for carbon-13 when compared at similar temperatures and magnetic fields. Some very spectacular results have been reported, including enhancements of factors of several thousand for carbon-13. There are results for nitrogen-15 that are even more impressive. However, there are disadvantages to DNP, both in general, and as specifically implemented in current commercial designs. First, DNP requires addition of a free radical species at a concentration adequate to yield efficient polarization in the solid state. Partly because of the spin relaxation contributions of the free radical, applications have been largely limited to observations of $^{13}C$ even though the ultimate sensitivity for $^{1}H$ would be better. Second, DNP requires fairly complex instrumentation with capabilities for both NMR and continuous microwave irradiation at an appropriate frequency. Third, polarization can take a significant length of time even with the best instrumentation. And fourth, some rapid melting procedure is required if solution NMR observation is the objective.

Current commercial instrumentation is based on providing a separate lower field magnet that can use commonly available microwave sources, although some non-commercial ventures have chosen to develop specialized high frequency microwave sources. In the commercial device, transfer of the sample to the observation magnet and melting of the sample is accomplished by flushing the polarization chamber with a large volume of warm solvent (typically 4 ml). This procedure results in undesired dilution of the sample and substantial loss of sensitivity (only 100 μl are used for observation in our highest sensitivity NMR probes). Solvents commonly used for this procedure are also non-aqueous. In addition, the current procedure limits sample polarization to one sample at a time, resulting in preparation of as few as one sample per hour. Similar limitations occur for the other sensitivity enhancement methods (the need for reactive reagents, complex instrumentation, etc). All of these factors suggest that additional options for sensitivity enhancement should be explored. For a subset of important biological applications of NMR, it would be of significant benefit to increase the sensitivity of NMR techniques, even by as little as an order of magnitude, if this could be done with simpler apparatus and procedures.

SUMMARY OF THE INVENTION

The present invention aims to provide an improvement to nuclear magnetic resonance spectrometers that increases the sensitivity of NMR techniques. More particularly, the present invention aims to provide such an improvement that increases the sensitivity of NMR techniques by an order of magnitude, applicable at least for a subset of biological applications of NMR. The invention contemplates such an improvement that facilitates or enhances NMR sensitivity using just low temperature polarization. The improvement is preferably an inexpensive and easy modification to an NMR spectrometer apparatus. The invention further aims to provide an associated method that improves the efficiency of data collection via an NMR apparatus that can simultaneously polarize and manipulate multiple samples.

Nuclear magnetic resonance (NMR) spectroscopy has many advantages, including its universal applicability as a non-destructive tool for analysis of compounds containing suitable magnetic nuclei, the near quantitative relationship between resonance intensity and molecular abundance, and the sensitivity of NMR observables to molecular structure. It suffers severely, however, from limited sensitivity. The present invention sets forth a solution to the problem that can increase sensitivity by an order of magnitude for a subset of applications including some important biological applications of NMR. The invention involves a simple device that can be fitted to most NMR spectrometers, exploiting well known enhancements of polarizations at low temperatures and an ability to rapidly transition from a frozen to a solution sample for observation. Application is best suited to time sensitive experiments in which spectra need to be collected within seconds of the melting transition. These potential applications include analysis of deuterium content of peptides in which deuterons rapidly back-exchange for solvent protons (something needed for a new resonance assignment procedure for large and glycosylated proteins), and real-time analysis of protein or RNA folding.

The device of the present invention is an upper stack for a nuclear magnetic resonance spectrometer apparatus. The device comprises a cryostat having at least one chamber for holding a plurality of samples, a sample loading tube extending to the cryostat, a sample ejection tube, and a sample changer mechanism, in part proximate to the cryostat, for moving specimens from the cryostat to an NMR probe.

The upper stack further comprises a drive mechanism for shifting the samples in the cryostat relative to the sample loading tube, to enable delivery of successive samples to the cryostat. The drive mechanism may take the form of a rotary drive, with the samples being disposed in a circular array inside the cryostat. The drive mechanism is configured to alternately index the samples into alignment with the sample loading tube and a sample extraction station.

The sample changer mechanism may include a carrier that is rotatable or shiftable alternately in two directions, namely, a first direction (e.g., vertical) for extracting a sample from the cryostat and a second direction (e.g., horizontal) for moving the extracted sample toward an axis of the NMR probe. The first direction is parallel to the axis of the cryostat, while the second direction is perpendicular to the axis. After positioning over the probe access tube a second parallel motion is executed in order to lower the sample to the probe.

Pursuant to an additional feature of the present invention, where the samples include specimen holders having caps or heads, the carrier includes a catch or detent engageable with heads of the samples for releasably entraining the specimen holders. The sample tubes themselves may also incorporate features to facilitate fast melting after transfer to the NMR probe. This could include platinum coating on the internal surface to facilitate inductive heating. This coating may be applied in special patterns to minimize loss of signal during observation. Caps may also be transparent to facilitate heating with laser radiation.

A method for gathering data using a nuclear magnetic spectrometer apparatus comprises, in accordance with the present invention, (i) subjecting a plurality of samples simultaneously to cryogenic temperatures in a cryostat disposed within the nuclear magnetic spectrometer apparatus, (ii) moving the cryogenically frozen samples in seriatim from the cryostat to an NMR probe of the nuclear magnetic spectrometer apparatus, (iii) heating each given sample while the given sample is disposed in the NMR probe, and (iv) immediately upon heating of each selected one of the samples, operating the nuclear magnetic spectrometer apparatus to obtain a spectrum from the selected one of the samples.

xxxIn accordance with a further feature of the present invention, the method further comprises rotating the cryostat about an axis and loading the samples in seriatim into the cryostat at a loading station. In that case, the moving of the cryogenically frozen samples in seriatim from the cryostat to a NMR probe includes the rotating samples about the axis.

The method may additionally comprise delivering a cryogenic fluid to the cryostat. The delivering may be effectuated at the loading station.

The heating of each given sample may be accomplished inductively by operating RF transmitter coils of the nuclear magnetic spectrometer apparatus. In that case, the samples are in specimen holders provided with a metallic layer, and the heating of each given sample includes inducing electrical current in the metallic layer of the respective specimen holder. Alternatively, the heating of each given sample includes directing a laser beam along an axis of the probe to the given sample in the NMR probe.

In accordance with yet another feature of the present invention, the moving of the frozen sample from the cryostat to the NMR probe includes shifting the samples in a first direction (e.g., vertically upwardly) from the cryostat, in a second direction toward an axis of the probe, and in a third direction along the axis into the probe.

The present invention provides an improvement to nuclear magnetic resonance spectrometers that increases the sensitivity of NMR techniques by an order of magnitude. The improvement is inexpensive and easy to install in an NMR spectrometer apparatus.

The present invention facilitates a general method for NMR resonance assignment of proteins isotopically enriched at sites occupied by specific amino acid sites. This contrasts with methods requiring uniform isotopic enrichment at all sites, something that is prohibitively expensive for proteins that must be expressed in mammalian cells. The general method includes measuring the rate of amide proton to amide deuteron exchange from the disappearance of various cross peaks in standard 15N-1H HSQC spectra of folded proteins, and correlating these rates with the disappearance of protons from derived peptides. The exchange is initiated by dissolving or diluting a protein in deutereated aqueous buffer and HSQC spectra are subsequently taken as a function of time. Aliquots are removed from the sample at various time points during exchange, exchange in the aliquots is quenched by lowering pH and temperature, and the aliquot is subjected to enzymatic digestion. Peptides from the aliquot (identified by mass spectrometry) are isolated by HPLC separation and returned to the spectrometer for analysis of amide proton peak intensity. The loss of intensity in particular amide peaks is inversely related to the deuterium content. In peptides from proteins labeled with isotopes in single amino acid types, isotope filtering of peptide spectra usually yields a single amide peak and deuteriium content that can be associated with an HSQC crosspeak from a specific sequential site in the protein. Because of the need to conduct analysis of peptides before back-exchange of deuterons, the process is best practiced in an integrated device that digests protein, fractionates peptides, quick freezes elution fractions, enhances NMR sensitivity through processes such as dynamic nuclear polarization, and returns samples quickly to a spectrometer for analysis. The present invention facilitates this procedure by polarizing directly the frozen samples and expediting the NMR spectral analysis steps.

A key advantage of a method and apparatus in accordance with the present invention is its simplicity. It is based on polarization enhancement inherent at low temperatures. Low temperature polarization is already used in DNP applications. It has been pointed out that many of the very high enhancements reported for DNP actually come partly from DNP and partly from the low temperature at which the electron polarization is established. For polarization at 2K in a 3.7 T magnetic field, the latter can contribute more than a factor of 100 to the reported enhancements. Direct enhancement of NMR sensitivity by polarization at low temperatures is not a new idea. It has been practiced in solids NMR in several instances. However, the coupling of non-DNP low-temperature polarization enhancement with rapid melting techniques and use of these in solution NMR is new.

A key advantage of a method and apparatus in accordance with the present invention is the minimization of instrument construction by making optimum use of hardware normally used in NMR data acquisition.

The present invention serves to increase sensitivity of NMR at the single acquisition level by an order of magnitude. To accomplish this and allow practical implementation in established laboratories, it is recommended that one uses the method and apparatus of the present invention to (1) achieve polarization at the highest fields available, (2) achieve polarization at temperatures of 10K or lower, (3) raise the ratio of data acquisition to polarization time to one FID per 5 minutes, and (4) employ a melting device that functions in less than a few seconds and does not require sample dilution.

A cost effective solution in accordance with the present invention thus achieves polarization in the magnetic field of the spectrometer to be used for data acquisition. This avoids the purchase of a separate polarizing magnet. An upper stack for a nuclear magnetic resonance spectrometer apparatus, in accordance with the present invention, preferably mates with probes currently used for high resolution NMR, including cryogenic probes and thus replaces the upper stack of an existing super conducting magnet. This will make the device generally applicable. These stacks normally carry airlines for variable temperature operation, sample ejection and sample spinning (no longer used in most high resolution applications). In some cases they make connections for pulsed field gradients and carry optical fibers for monitoring sample position and spinning. These normal or conventional functions are not shown in the Figures discussed below, but can easily be accommodated in the design.

An upper stack in accordance with the present invention can be fitted to most NMR spectrometers, exploiting well-known enhancements of polarizations at low temperatures and an ability to rapidly transition from a frozen to a solution sample for observation. Application is best suited to time sensitive experiments in which spectra need to be collected within seconds of the melting transition. These potential applications include analysis of deuterium content of peptides in which deuterons rapidly back-exchange for solvent protons (something needed for a new resonance assignment procedure for large and glycosylated proteins), and real-time analysis of protein or RNA folding.

DETAILED DESCRIPTION

Figure 1:
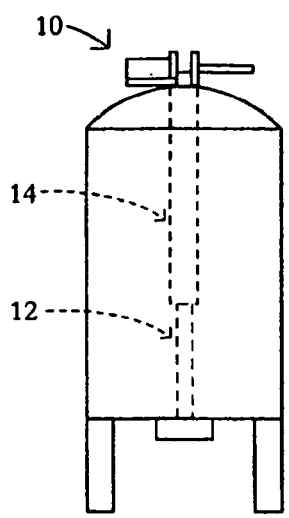
FIG. 1 is a schematic side elevational view of an NMR apparatus with an upper stack in place in accordance with the present invention.
Figure 2:
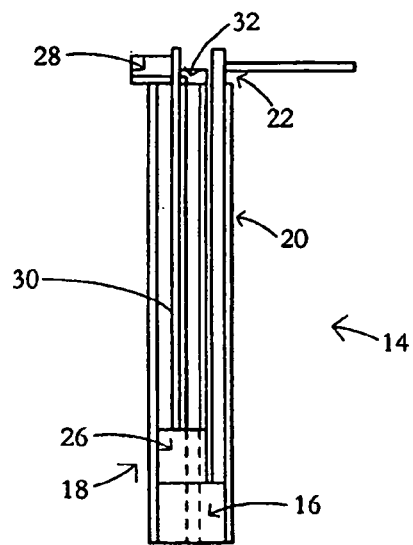
FIG. 2 is a schematic side elevational view, on a larger scale, of the upper stack shown in FIG. 1, depicting a toroidal sample-holding cryostat.

FIG. 1 diagrammatically depicts an NMR spectrometer magnet 10 including a probe 12 and an upper stack 14. As shown in FIG. 2, upper stack 14 comprises a rotatable helium cryostat 16, a sample changer mechanism 18, and an insulated outer stack tube 20. A helium delivery and sample loading tube 22 is disposed at an eccentric radial location and extends vertically through outer stack tube 20 to cryostat 16. Sample changer mechanism 18 includes a laterally shiftable frame or body member 26 and a drive box 28 with a drive train element 30, the latter extending downwardly from drive box 28 at an upper end of the stack 14 to sample changer member 26. An insulated sample ejection tube 32 extends coaxially through outer stack tube 20 from sample changer body member 26.

Figure 3:
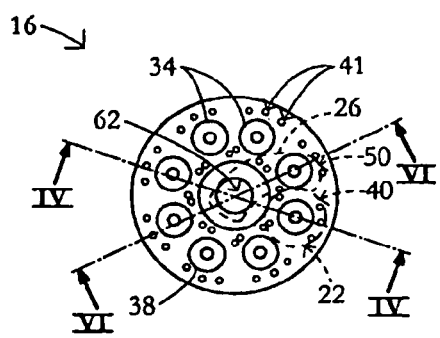
FIG. 3 is a schematic top plan view, on yet a larger scale, of the cryostat of FIG. 2.
Figure 4:
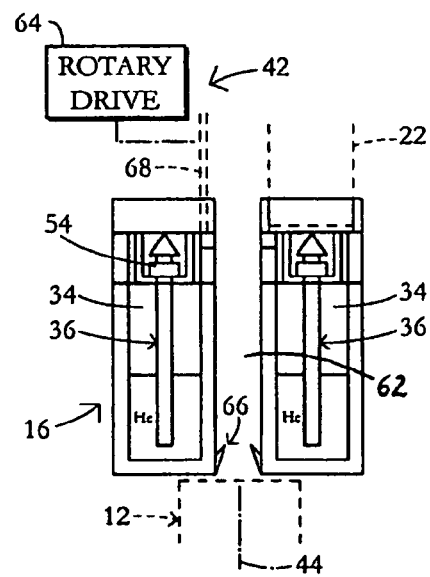
FIG. 4 is a schematic transverse cross-sectional view taken along line IV-IV in FIG. 3.
Figure 5:
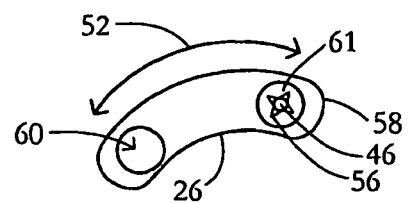
FIG. 5 is a schematic top plan view, on an even larger scale, of a sample changer member shown in phantom in FIG. 3.

As shown in FIGS. 3 and 4, crysostat 16 has seven chambers 34 for holding respective samples or specimens 36 and an eighth chamber 38 that functions as a port for receiving a cryogenic fluid (preferably helium) from helium delivery and sample loading tube 22 at a helium and sample loading station 40. Cryostat 16 is further provided with a network of helium return bores or holes 41. Sample changer member 26 is disposed proximate or adjacent to cryostat 16 for moving specimens from respective ones of chambers 34 to NMR probe 12.

Upper stack 14 further comprises a drive mechanism 42 for shifting cryostat 16 relative to sample loading tube 22, to enable delivery of successive samples to respective chambers 34 at loading station 40. Drive mechanism 42 includes a rotary drive 64 and a drive rod 68 extending to cryostat 16, the sample-holding chambers 34 and helium port 38 of the cryostat being disposed in a circular array about an axis of rotation 44, as shown in FIG. 3. Drive mechanism 42 is configured to alternately index sample-holding chambers 34 and helium-receiving port 38 into alignment with sample loading tube 22 at loading station 40.

As depicted in FIG. 4, sample-holding chambers 34 are elongate and are oriented parallel to cryostat rotation axis 44. Port 38 is likewise an elongate ancillary chamber extending parallel to the sample-holding chambers 34 and axis 44.

Sample changer mechanism 18 includes a carrier rod 46 movably mounted to frame or body member 26 and shiftable alternately in two directions, namely, (i) an upward direction 48 for extracting a sample or specimen 36 from a chamber 34 at a sample extraction station 50 and (ii) a lateral or horizontal direction 52 for moving the extracted sample toward cryostat rotation axis 44, which is also the axis of NMR probe 12. The first carrier-movement direction 48 is parallel to sample-holding chambers 34 and axis 44, while the second carrier-movement direction 52 is along a circular path in a plane perpendicular to the chambers and axis 44.

Samples or specimens 36 include specimen holders (not separately designated) having caps or heads 54. Carrier 46 includes one or more catches, detents or prongs 56 engageable with heads 54 of the samples 36 for releasably entraining the samples. Sample changer body member 26 is disposed at a first location relative to frame or cryostat 16 with an extraction or access channel 61 over a sample chamber at extraction station 50. Channel 60 of sample changer body member 26 is simultaneously aligned with access to the probe 12 and ejection tube 32. Body member 26 along with sample carrier 46 can move to a second location spaced from the first location, with channel 61 now alignable with the NMR probe 12 and sample ejection tube 32. Carrier 46 can move downward in this position to release the sample to the probe. Once body member 26 returns to the first position, melting and data collection can proceed, the spectrometer bore 32 can be used to eject the sample, and cryostat 16 can rotate to align a new sample chamber 34 with access channel 61. The process can then be repeated.

Polarization of samples 36 is achieved by virtue of the disposition of cryostat 16 in a high field region of the NMR data acquisition magnet 10 of the NMR spectrometer. Superconducting magnets used in NMR have high magnetic fields that extend above and below the region in which the rf coil of the NMR probe 12 is located. Data supplied by Varian, Inc., on the field profile for an 89 mm 600 MHz magnet indicate a decrease in field of less than 5% in the region within 150 mm from the center of the magnet. This provides adequate space, outside the active region of probe 12 to accomplish polarization at a high magnetic field (18 T for an 800 MHz magnet and 11 T for a 500 MHz magnet).

Samples 36 are subjected to sufficiently low temperatures where He delivery and sample loading tube 22 (FIG. 2) conveys a continuous flow of liquid He, as in a commercial device made by Oxford Instruments specifically for NMR use. This device includes a He pump, flow control, temperature monitoring and a vacuum jacketed back-flow cooled delivery tube that allows sample access to common NMR probes. The unit is intended for operation down to 4K and comes with delivery tube options designed for standard NMR bore sizes, for instance, a 51 mm delivery tube with 30 mm sample access and a 31 mm tube with 10 mm sample access.

Cryostat 16 is a vacuum shielded toroidal He cryostat. The interface between delivery and sample loading tube 22 and He cryostat 16 may be adapted to mesh with the Oxford design.

Cryostat 16 is capped with an insulating sample holding plate (not shown) that has drive teeth cut into the outer edge of a recessed ring surrounding a probe access and sample eject hole 62. The cryostat and cap rotate to position sample chambers 34 under helium delivery and sample loading tube 22 at loading station 40. Above cryostat 16 is a fixed liquid nitrogen cooled plate (not shown) that positions helium delivery and sample loading tube 22, positions the chive rod of drive mechanism 42, and has a guide slot for movement of the sample changer body member 26 (with holes 60, 58 at the center and extreme to allow alternate access to one sample chamber 34 and probe access and sample eject hole 62). The design may be scaled to operate with 3 mm NMR tubes in a 63 mm bore magnet. The accommodation of multiple samples 36 in the high field cryostat 16 is intended to increase throughput of a device that is likely to be limited by time required for polarization. With seven samples and a 35 min polarization time, one acquisition can be achieved every 5 minutes.

Figure 6:
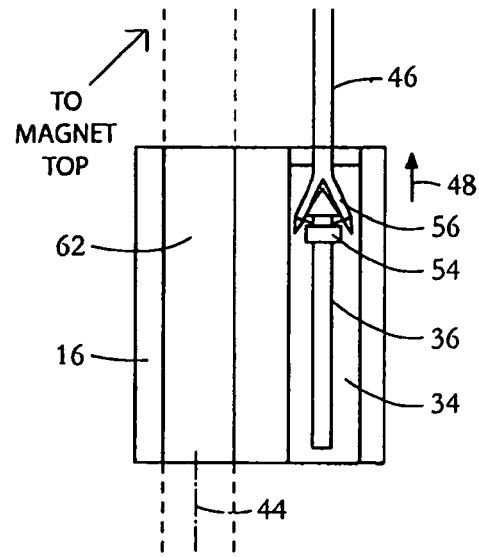
FIG. 6 is a schematic partial cross-sectional view, taken along line VI-VI in FIG. 3, showing a sample carrier element of the sample changer.

Sample changer body member 26 slides from a sample pick position shown in phantom lines in FIG. 3, in which the sample chamber 34 at sample extraction station 50 adjacent to helium delivery and sample loading tube 22 is accessible, to a sample drop position in which the sample pick carrier or rod 46 is vertically aligned with the NMR probe 12. Sample pick carrier or rod 46 can be pushed down on the sample cap or head 54 (FIG. 6) of the sample or specimen 36 to be extracted and down sample probe access and sample eject hole 62 in cryostat 16 to NMR probe 12. As indicated above, sample pick carrier or rod 46 is equipped with catches, detents or prongs 56 that automatically clip to a specially designed sample cap 54 on downward pressure in the pick position and automatically release when pushed against prongs 66 (FIG. 4) just above the NMR probe 12 in the sample drop position. Both the sliding of the changer body member 26 and the vertical motion of the sample carrier or rod 46 are driven by pneumatics or stepper motors (not separately shown) mounted in drive box 28 at the top of the magnet apparatus 10. On return of the sample carrier or rod 46 to the pick position at sample extraction station 50, without a sample attached, an unobstructed passageway connects probe access and sample eject hole 62 in cryostat 16 to the upper room temperature bore hole. This allows normal VT operation of the NMR probe 12 and normal pneumatic sample ejection (not shown is a central sleeve with holes for sample eject nitrogen). Ejected samples are captured in a tray (not illustrated) at the top of the magnet 10.

Figure 7:
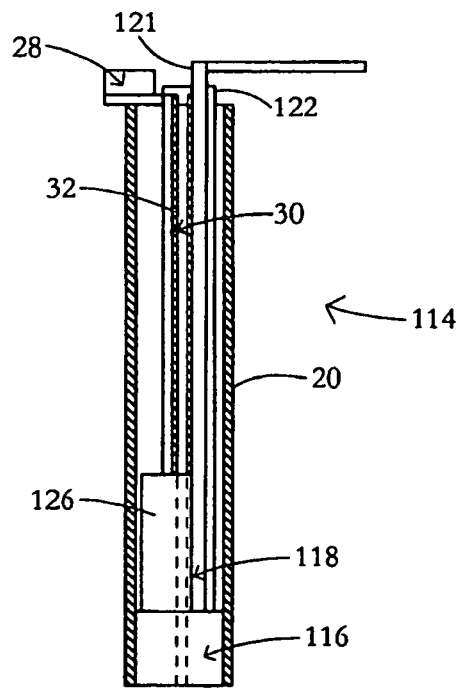
FIG. 7 is a schematic side elevational view, similar to FIG. 2 on an even larger scale, of another embodiment of an upper stack in accordance with the present invention, also depicting a toroidal sample-holding cryostat.

FIG. 7 diagrammatically depicts an NMR upper stack 114 similar to upper stack 14 of FIGS. 1-6. Identical reference numerals have been used to designate identical or substantially identical structures.

Upper stack 114 comprises a rotatable helium cryostat 116, a sample changer mechanism 118, and insulated outer stack tube 20. A cryogenic helium delivery and return tube 121 and a sample loading tube 122 are disposed at an eccentric radial location and extend vertically through outer stack tube 20 to cryostat 116. Sample changer mechanism 118 includes a rotatable sample changer body member 126, together with drive box 28 and tubular drive train housing 30, the latter extending downwardly from drive box 28 at an upper end of the stack 114 to sample changer body member 126. Insulated sample ejection tube 32 extends coaxially through outer stack tube 20 from sample changer body member 126.

Figure 8:
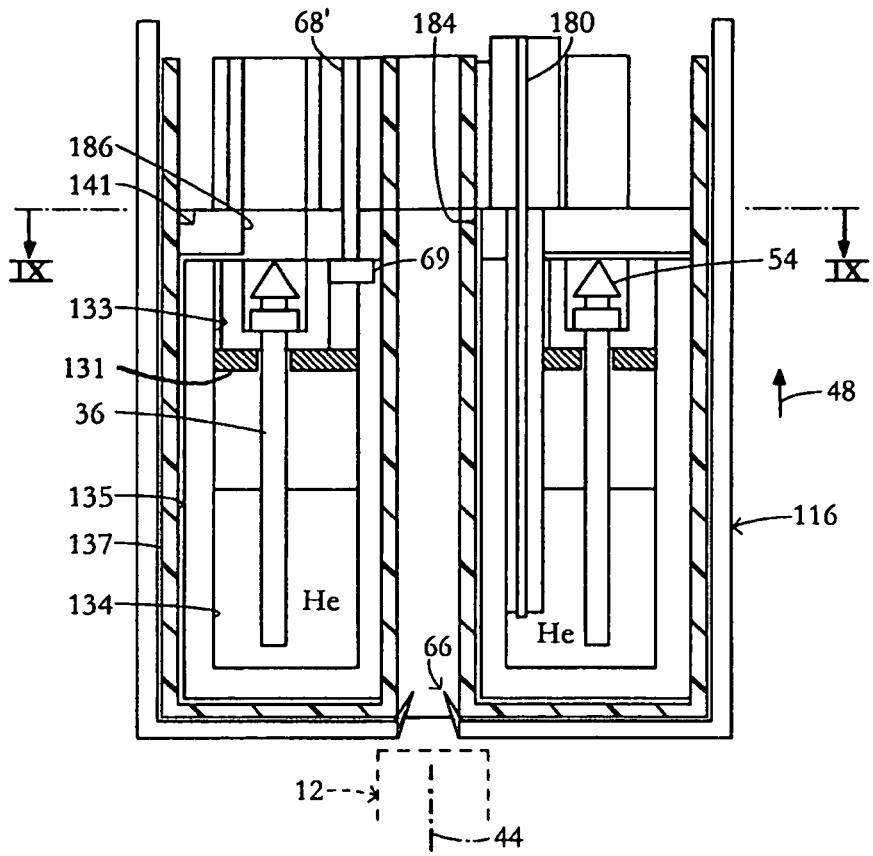
FIG. 8 is a schematic vertical or longitudinal cross-sectional view, on yet a larger scale, of a cryostat shown in FIG. 7.
Figure 9:
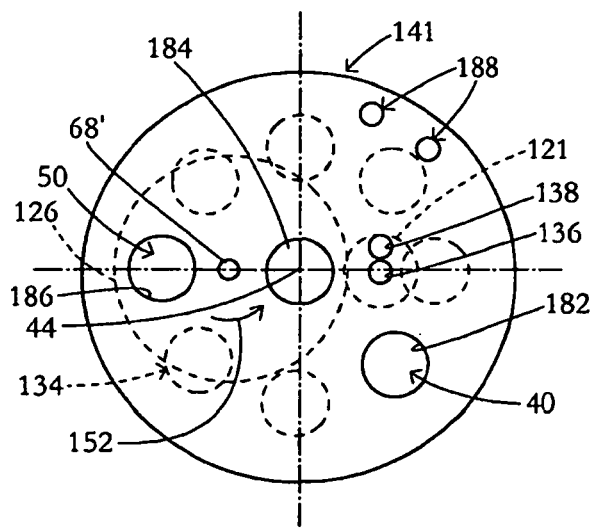
FIG. 9 is a schematic top plan view, taken along line IX-IX in FIG. 8, of a nitrogen-cooled plate located above the cryostat of FIG. 8.

As shown in FIGS. 8 and 9, crysostat 116 has a plate 131 that holds a sample cassette 133 that has a single toroidal chamber 134 for holding eight samples or specimens 36. The chamber 134 is surrounded by a toroidal dewar 135 and a toroidal insulation member 137. Cryogenic delivery and return tube 121 delivers a cryogenic fluid (preferably helium) to the cryostat 116 through a central channel 180 and provides a return path outside this central channel. (The central channel extends through a first bore or passageway 136 in a nitrogen-cooled plate 141, see below, while the return path extends through a second bore or passageway 138 in that nitrogen plate.) Sample changer body member 126 is disposed proximate or adjacent to cryostat 116 for moving specimens from chamber 134 to the NMR probe 12.

Upper stack 114 incorporates drive mechanism 42 including a central drive rod or shaft 68' and a terminal gear 69 (FIG. 8) for rotating sample cassette 133 about vertical axis 44, to enable delivery of successive samples from loading tube 122 (FIG. 7) to chamber 134 at loading station 40 (FIG. 9). Samples 36 are held inside cryostat 116 by cassette 133 and disposed in a circular array (FIG. 8) about rotation axis 44. Drive mechanism 42 is configured to alternately index samples 136 into alignment with sample loading tube 122 at loading station 40.

As depicted in FIG. 8, sample-holding chamber 134 has an elongate half cross-section oriented parallel to sample cassette rotation axis 44. In other words, chamber 134 is coaxial with axis 44, sample ejection tube 32 and NMR probe 12. Owing to rotation of sample cassette 133 about axis 44, each sample 136 is successively aligned with sample loading tube 122 at loading station 40.

As discussed hereinabove with reference to sample changer mechanism 18, sample changer mechanism 118 includes carrier rod 46 (FIG. 10), which is movably mounted to sample changer body member 126 and shiftable alternately in two directions, namely, (i) upward or vertical direction 48 (FIG. 9) for extracting a sample or specimen 36 from chamber 134 at a sample extraction station 150 and (ii) along a circular path 152 in a horizontal plane (FIGS. 8 and 10) for moving the extracted sample toward the cryostat rotation axis 44 (also the axis of NMR probe 12).

Figure 10:
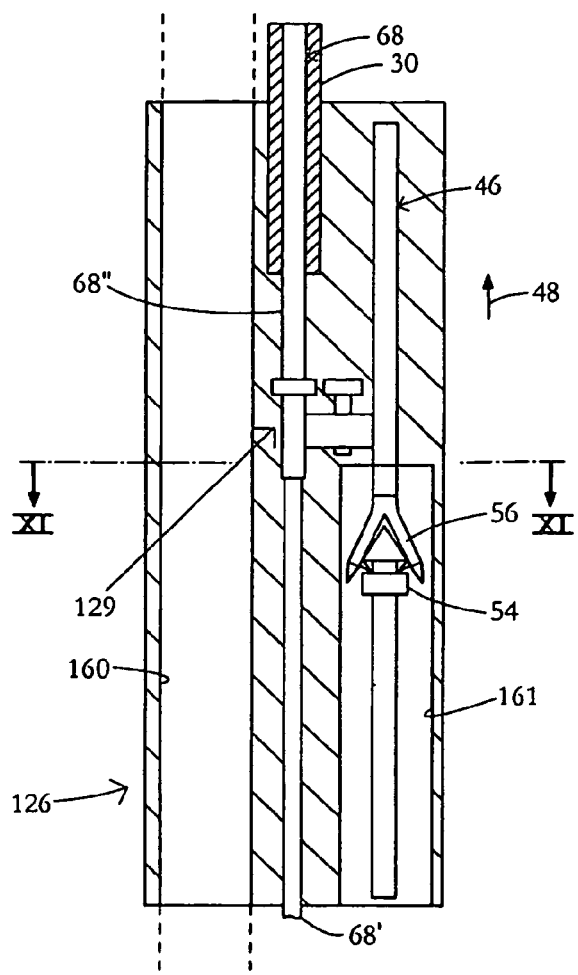
FIG. 10 is a schematic vertical or longitudinal cross-sectional view, on a larger scale, of a sample changer member shown in FIGS. 7 and 9.
Figure 11:
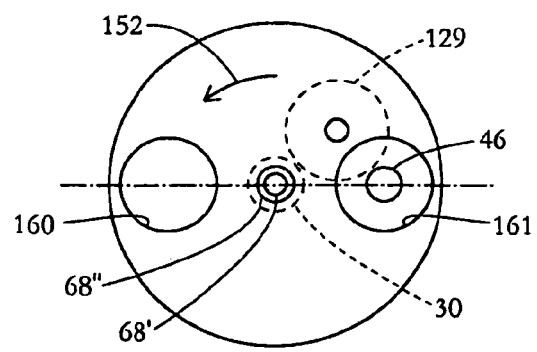
FIG. 11 is a schematic transverse cross-sectional view, taken along line XI-XI in FIG. 10.

With reference in part to FIGS. 10 and 11, sample changer body member 126 is disposed at a first location relative to frame or cryostat 116 with an extraction or access channel 161 located over a sample 136 at extraction station 150. A through channel 160 of sample changer body member 126 is simultaneously aligned with probe 12 and ejection tube 32. Body member 126, along with sample carrier 46, is rotatable along circular path 152 (FIGS. 9 and 11) by drive box 28 and drive train element 30 (FIG. 7) acting via a worm drive 129 at a lower end of an outer tubular drive member 68" of drave 68.

Rotation of body member 126 brings sample carrier 46, as well as an entrained sample, to a second location spaced from the first location, with channel 161 now aligned with the NMR probe 12 and sample ejection tube 32. Carrier 46 is controllable to move downward at this position to release the sample to the probe 12. Once body member 126 returns to the first position, melting and data collection can proceed. After melting and data collection, the spectrometer bore 32 can be used to eject the sample, and the sample cassette 133 in cryostat 116 can rotate to align a new sample 136 with access channel 161. The process can then be repeated.

Polarization of samples 36 in cryostat 116 is achieved as discussed above with respect to the first embodiment.

Samples 36 are subjected to sufficiently low temperatures where He delivery and sample loading tube 122 (FIG. 7) conveys a continuous flow of liquid He, as in a commercial device made by Oxford Instruments specifically for NMR use. As discussed above, this device includes a helium pump, flow control, temperature monitoring and a vacuum jacketed back-flow cooled delivery tube that allows sample access to common NMR probes. The unit, intended for operation down to 4K, comes with delivery tube dimensions appropriate for the device of FIGS. 7-11.

Cryostat 116 is a vacuum shielded toroidal He cryostat. The interface between delivery and sample loading tube 122 and He cryostat 116 may be adapted to mesh with the Oxford design.

Cryostat 116 includes, in an upper region thereof, a fixed liquid nitrogen cooled plate 141 that positions helium delivery tube 121, sample loading tube 122, and bipartite drive rod 68 for rotating drive mechanism 42 and sample changer body member 126. Nitrogen-cooled plate 141 has holes 182 and 184 respectively aligned with sample delivery tube 122 at loading station 40 and with probe 12 and ejection tube 32 along axis 44. Nitrogen-cooled plate 141 also has a hole 186 at sample extraction station 150 (where samples 36 are removed or extracted from chamber 134 by carrier rod 46). Holes 188 correspond to delivery and return channels for nitrogen.

As described above, the design of FIGS. 7-11 may be scaled to operate with 3 mm NMR tubes in a 63 mm bore magnet.

Sample changer body member 126 (shown in phantom lines in FIG. 9) rotates to align a selected sample 136 to a sample drop position in which the sample pick carrier or rod 46 is vertically aligned with the NMR probe 12. As discussed above with reference to FIGS. 1-6, sample pick carrier or rod 46 can be pushed down on the sample cap or head 54 (FIG. 9) of the sample or specimen 36 to be extracted and down sample probe access and sample eject hole 32 in cryostat 16 to NMR probe 12. As further indicated above, sample pick carrier or rod 46 is equipped with catches, detents or prongs 56 that automatically clip to a specially designed sample cap 54 on downward pressure in the pick position and automatically release when pushed against prongs 66 (FIGS. 4, 9) just above the NMR probe 12 in the sample drop position. Both the rotating of the changer body member 126 and the vertical motion of the sample carrier or rod 46 are driven by pneumatics or stepper motors (not separately shown) mounted in drive box 28 at the top of the magnet apparatus 10. On return of the sample carrier or rod 46 to the pick position at sample extraction station 150, without a sample attached, an unobstructed passageway connects probe access and a sample eject hole in cryostat 116 to the upper room temperature bore hole. This allows normal VT operation of the NMR probe 12 and normal pneumatic sample ejection (not shown is a central sleeve with holes for sample eject nitrogen). Ejected samples are captured in a tray (not illustrated) at the top of the magnet 10.

Data acquisition of a sample in the NMR probe 12 is initiated after melting of the sample. This melting must be achieved in a time short compared to the shortest spin lattice relaxation time encountered in either the warming solid or the melted solution. Relaxation times in the solid are long for most samples, and relaxation times in melted samples should be acceptable. For protons in macromolecules at high magnetic field, these can be several seconds. For smaller molecules it may be more practical to store polarization in a heteronucleus ($^{13}$C) by cross polarization before melting. $^{13}$C spin relaxation for small molecules in melted samples can be tens of seconds. In the latter case, observation can still be via protons using solution phase INEPT transfers. In either case, targeting a melting time on the order of one or two seconds seems advisable.

There are two approaches to rapid heating of samples. The first is inductive heating. This is the simplest approach. This has the advantage that no additional hardware is required. The tubes or ampoules for the samples 36 are coated with an appropriate conductor (platinum—Pt—has an appropriate conductivity for this application). RF energy is applied to the sample using the transmitter and coils normally present in an NMR spectrometer, and induced currents in the Pt coating heat the sample. A rise in temperature of 100K can be achieved in cold samples in less than ten seconds using relatively high powers and a tube coated on the outside. Alternatively specimen tubes or ampoules may be coated on the inside. (A Pt dispersion is painted on the inside of a tube and the tube placed in an glass annealing oven for a few minutes.) The coatings are ideally on the order of a micron. Even with a continuous coating, loss in sensitivity appears to be less than 20%. It may be possible to apply a coating in a geometric design, which may minimize $B_1$ coupling to the coating and minimize sensitivity loss. Using an ethylene glycol temperature standard and about 2 watts continuous rf at 125 MHz in a 500 MHz spectrometer one can achieve a 30K rise in a 300 μl sample in 16 s. This is just 1% of the available rf power at this frequency, and heating rates could in principle be increased significantly.

The second approach to rapid heating of samples utilizes a $CO_2$ laser. This approach avoids the need for a Pt coating on NMR tubes, avoids any associated signal loss or sample incompatibility, and may be faster. Laser heating from outside an NMR tube wall of 100K in less than 1 s has been achieved. The calculated power requirement for heating and melting a largely aqueous 100 μl sample in 4 s starting at 4 k is 25 W. IR lasers in this power range are commercially available. The clearest path for delivering radiation from a laser to a sample 36 in the NMR probe 12 is from the top of the magnet 10. The laser can be mounted directly overhead and pointed down the open path of sample ejection tube 32 to the sample in NMR probe 12. A parabolic mirror can also be mounted on the plate at the top of the upper stack 14 and the laser mounted more remotely to focus the beam and direct it to the sample. Many NMR probes (including cryogenic probes) also have an open path from the bottom of the probe to the sample. Thus, mounting a parabolic mirror at the bottom of the probe remains an option. Lasers in this power range require suitable curtains around the instrumentation and restricted access.

Control of the laser and sample changer mechanism 18 or 118, along with sample ejection and triggering of the acquisition sequence, is under program control. Occupancy of sample chambers 34 or chamber 134, occupancy of the NMR probe 12, and occupancy of the eject tray (not shown) may be monitored with suitable optical devices. The temperatures of cryostat 16 or 116 and NMR samples 36 may be monitored via suitable sensors.

A method for gathering data using nuclear magnetic spectrometer apparatus 10 comprises (i) subjecting a plurality of samples 36 simultaneously to cryogenic temperatures in cryostat 16 or 116, (ii) moving the cryogenically frozen samples 36 in seriatim from the cryostat to NMR probe 12, (iii) heating each given sample 36 while the given sample is disposed in the NMR probe, and (iv) immediately upon heating of each selected sample, operating the nuclear magnetic spectrometer apparatus 10 to obtain a spectrum from the selected sample.

The circular array of samples 36 in cryostat 16 or 116 is rotated about axis 44 and samples 36 are conveyed in seriatim into respective chambers 34 or chamber 134 of the cryostat at loading station 40. (In the embodiment of FIGS. 7-11, the body or casing of cryostat 116 remains stationary, while sample cassette 133 with the samples 36 carried thereby rotates under the action of drive rod or shaft 68' and gear 69.) Moving the cryogenically frozen samples 36 in seriatim from cryostat 16 or 116 to NMR probe 12 includes rotating cryostat 16 about axis 44—so that a target sample or specimen 36 moves about a circular path from sample loading station 40 to sample extraction station 50 or 150.

Cryogenic fluid, that is, liquid helium, is delivered to cryostat 16 or 116 and particularly to a helium receiving port 38 or passageway 136 in the cryostat. In the embodiment of FIGS. 7-11, liquid helium may be delivered via channel 180 and passageway 136 to sample-receiving chamber 134 in seriatim during rotation of the sample cassette 133.

As indicated above, the heating of each given sample 36 may be accomplished inductively by operating RF transmitter coils of the nuclear magnetic spectrometer apparatus 10. In that case, the samples 36 are in specimen holders or tubes provided with a metallic (e.g. Pt) layer, and the heating of each given sample includes inducing electrical current in the metallic layer of the respective specimen holder or tube. Alternatively, the heating of each given sample includes directing a laser beam along an axis 44 of the NMR probe 12 to the given sample 36 in the NMR probe.

The moving of a frozen sample 36 from cryostat 16 or 116 to NMR probe 12 includes shifting the samples 36 in a first direction vertically upwardly from the respective chambers 34 of the cryostat, in a second direction horizontally inwardly toward rotation and probe axis 44, and in a third direction vertically downwardly along the axis 44 into the probe 12.

The above-described approach to enhanced polarization and analysis of small molecules has utility in a particularly challenging type of biological application, namely, one in which there is not only a requirement for sensitivity enhancement, but one in which there is a time constraint on data acquisition. Enhancements are used to maximum advantage when data are collected in a single acquisition after polarization enhancement. This is because restoration of polarization in the solid state (samples frozen at 4K), if not driven in some way, can take a long time, something on the time scale of $T_1$ spin relaxation. A number of spin relaxation studies as a function of temperature and magnetic field have been conducted over the years. Recent investigations show proton $T_1$s lengthening with decreases in temperature and increases in magnetic field to tens of seconds at 10K and 1.4 T. Heteronuclear $T_1$s would be correspondingly longer. The processes appear to be dominated by methyl rotations at low temperature and hence are quite sample dependent. However, extrapolation to higher fields would suggest timescales on the order of 5-10 minutes at 6K and 18.7 T for protons and hours for heteronuclei. This means that time averaging of signals in the usual sense would be impractical.

One application requiring rapid acquisition at high sensitivity stems from the demands of the inventors' own research. Recently the inventors have introduced a new NMR resonance assignment strategy, one applicable to proteins for which uniform isotopic labeling with $^{15}N$, $^{13}C$, and $^2H$ is not practical. This is relevant to a large class of proteins. It includes proteins that cannot be expressed in bacterial hosts, including most glycoproteins and proteins requiring specific chaperones for folding. Such proteins constitute more than half of all mammalian proteins and nearly all proteins prepared for therapeutic applications.

The method relies on labeling with specific $^{15}N$-amino acids and correlating amide proton exchange rates in the folded protein with deuterium content at specific sites in peptides derived from the protein. Dissolving the 15N-labeled protein in deuterated buffer and monitoring the time course of disappearance of 15N-1H HSQC cross-peaks easily yields amide exchange rates in the folded protein. The rates range from a few times per minute to a few times per week and are easily measured with conventional NMR hardware. For peptides the initial intent was to both sequence the peptides and measure deuterium content at specific sites using mass spectrometry. The peptides are made by extracting aliquots at various times during exchange, quenching the exchange by lowering temperature and dropping the pH, digesting the protein quickly with pepsin, and separating the peptides by fast HPLC. Sequencing by mass spectrometry works well. However, problems with deuterium scrambling during ionization, and lack of sequence coverage on digestion, prevent analysis of deuterium content at specific sites. This dictated a return to analysis of peptides by NMR. Here, the deuterium content at the labeled sites is analyzed by $^{15}N$-filtered NMR, where resonance intensity loss can be associated with deuteration at a specific $^{15}N$-labeled site. The rates of exchange determined from the peptides are then correlated with rates from HSQC cross-peak measurements to make the cross-peak assignment.

While the procedure works, the analysis of the peptides is very demanding in terms of NMR sensitivity and the ability to acquire data rapidly. Deuteriums in the peptides actually start to back-exchange for protons in the solvent from the point of exchange quenching onward. Even a 5° C. and pH 3 some sites back-exchange with half times of ten minutes or less. Digestion and separation have been reduced to this time scale, but NMR acquisition remains problematic. The quantities of peptide are on the order of 10 μg and acquisitions often take longer than 30 min on available spectrometers of the highest sensitivity. The ideal situation, enabled by the present invention, is to freeze all samples to 77K (with liquid nitrogen) immediately on collection from the HPLC, transfer them frozen to a cryostat in the high field of an NMR magnet, melt these just before data acquisition, and collect data at high sensitivity in just a single acquisition (actually a train of spin echoes after a single 90° pulse). Low temperature polarization followed by melting, and acquisition with an order of magnitude increase in sensitivity is well suited to this mode of acquisition. A train of 9 echoes following a single observe pulse at 10 times the sensitivity is equivalent to approximately the 900 pulses taken over 30 min in a standard acquisition.

A second area of application of the present invention is in the monitoring of biological processes that occur on the timescales of seconds. Among target processes are folding of nucleic acids and proteins. These processes lie at the heart of many basic biological mechanisms, but they have come to light recently because of diseases linked to mis-folding of many proteins. For example, the many mutants of the chloride channel linked to cystic fibrosis are actually mutations that alter the rate or sequence of proper folding, and not dysfunction of the protein itself. Various forms of fast acquisition have been reviewed recently and suggested to be appropriate in monitoring folding processes in RNAs. For example, the folding of RNAseP, a ribozyme that cleaves tRNA precursors is known to populate intermediates on the way from unfolded to folded. The step from the intermediate to the folded form occurs on time scales from less than a second to a minute depending on temperature. Most studies have been done using optical monitoring or 1D NMR, often triggering folding by the photolytic release of caged divalent cations. Folding processes in proteins have also been observed, some even using multidimensional NMR when processes are slow. However, many process of interest are fast and only 1D NMR has been used for observation. Monitoring fast processes by 2D $^{15}$N HSQC spectra would clearly provide more useful structural information on intermediates. Here unfolded versus various forms of folded proteins and nucleic acids are easily distinguished. The problem is acquisition of HSQC spectra on the timescale of seconds.

Single pulse acquisition of HSQC spectra has in fact been demonstrated. The procedure is based on spatial resolution of different regions of a sample, allowing these regions to provide the frequency resolution for a second dimension. The procedure, as originally described, requires highly concentrated samples and would not be applicable to biological samples such as those suggested above. However, coupling with sensitivity enhancement by DNP has recently been demonstrated using $^{15}$N labeled urea. This clearly puts sensitivity in the range of applicability to protein and RNA solutions, but it is as yet unclear if the addition of free radicals, required for polarization at much higher concentrations, and melting with non-aqueous solvents, would be compatible with these samples. Enhancement by low temperature polarization is more likely to be compatible. For cases where divalent cations (RNA) or changes in pH (proteins) initiate folding, one can envision quick-freezing a mixture of RNA or protein and appropriate folding buffer after a variable period of time. Samples could then be polarized at low temperatures in the spectrometer, quickly melted, and analyzed by single pulse HSQC spectra. Alternately, one could capitalize on cold denaturation for proteins and allow refolding to be initialed on melting. Observations can then be made by one pulse HSQCs at time points within the spin relaxation time of the stored magnetization (tens of seconds if storage on heteronuclei is used).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. An upper stack for a nuclear magnetic resonance spectrometer apparatus having an axis, said upper stack being disposable on said axis as an integral part of said spectrometer apparatus, said upper stack comprising:
    a cryostat having at least one sample-receiving chamber for holding a plurality of samples in respective sample holders;
    a sample loading tube extending to said cryostat;
    a sample ejection tube; and
    a sample changer mechanism disposable at least in part proximate to said cryostat for moving samples in said respective sample holders from said at least one chamber to an NMR probe at least in part through an on-axis movement.

2. The upper stack defined in claim 1, further comprising a drive mechanism for shifting said specimens relative to said sample loading tube, to enable delivery of successive samples to said cryostat.

3. The upper stack defined in claim 2 wherein said drive mechanism is a rotary drive, said samples being disposed in a circular array in said cryostat, said drive mechanism being configured to alternately index said samples into alignment with said sample loading tube.

4. The upper stack defined in claim 3 wherein said cryostat includes a port or passageway for receiving a cryogenic fluid, said cryogenic fluid being conveyed to said port or passageway via said a delivery tube.

5. The upper stack defined in claim 1 wherein said sample changer mechanism includes a carrier shiftable for extracting a sample from said cryostat and for moving the extracted sample toward an axis of the NMR probe.

6. The upper stack defined in claim 5 wherein said carrier is shiftable in a first direction parallel to said axis to extract a sample from said cryostat and in a second direction perpendicular to said axis to move the extracted sample toward an axis of the NMR probe.

7. The upper stack defined in claim 6 wherein said samples include specimen holders having caps or heads, said carrier including a catch or detent engageable with heads of said samples for releasably entraining said specimen holders.

8. The upper stack defined in claim 7 wherein said sample changer mechanism includes a frame or body, said carrier being disposed at a first location relative to said frame or body member, said frame or body member being provided with a channel at a second location spaced from said first location, said channel being alignable with the NMR probe.

9. The upper stack defined in claim 8 wherein said channel is alignable with said probe while said carrier is simultaneously alignable with one of said specimen holders, said samples being located in said cryostat at a radial distance from an axis of rotation of said cryostat, said channel being disposed at said distance from said carrier.

10. The upper stack defined in claim 8 wherein said channel is alignable with said probe leaving a clear path to the sample in the probe for heating with a laser beam while said carrier is simultaneously alignable with one of said specimen holders.

11. The upper stack defined in claim 1 wherein said cryostat includes a sample-supporting cassette.

12. A method for gathering data using a nuclear magnetic spectrometer apparatus, comprising:
    loading a plurality of samples into a cryostat disposed with the nuclear magnetic spectrometer apparatus, the loading of said samples including rotating said cryostat about an axis and loading said samples in seriatim into said cryostat at a loading station;
    subjecting said plurality of samples simultaneously to cryogenic temperatures in said cryostat disposed within the nuclear magnetic spectrometer apparatus;
    moving the cryogenically frozen samples in seriatim from said cryostat to a NMR probe of the nuclear magnetic spectrometer apparatus;
    heating each given sample while the given sample is disposed in the NMR probe; and immediately upon heating of each selected one of said samples, operating the nuclear magnetic spectrometer apparatus to obtain a spectrum from said selected one of said samples.

13. The method defined in claim 12 wherein the moving of the cryogenically frozen samples in seriatim from said cryostat to a NMR probe includes the rotating of said samples about said axis.

14. The method defined in claim 12, further comprising delivering a cryogenic fluid to said cryostat, said delivering being effectuated during loading of samples into said cryostat at said loading station.

15. A method for gathering data using a nuclear magnetic spectrometer apparatus, comprising:
   subjecting a plurality of samples simultaneously to cryogenic temperatures in a cryostat disposed within the nuclear magnetic spectrometer apparatus;
   moving the cryogenically frozen samples in seriatim from said cryostat to a NMR probe of the nuclear magnetic spectrometer apparatus;
   heating each given sample while the given sample is disposed in the NMR probe; and
   immediately upon heating of each selected one of said samples, operating the nuclear magnetic spectrometer apparatus to obtain a spectrum from said selected one of said sample,
   wherein the heating and melting of each said given sample is accomplished inductively by operating RF transmitter coils of the nuclear magnetic spectrometer apparatus.

16. The method defined in claim 15 wherein the samples are in specimen holders provided with a metallic layer, the heating and melting of each said given sample includes inducing electrical current in the metallic layer of the respective specimen holder.

17. A method for gathering data using a nuclear magnetic spectrometer apparatus, comprising:
   subjecting a plurality of samples simultaneously to cryogenic temperatures in a cryostat disposed within the nuclear magnetic spectrometer apparatus;
   moving the cryogenically frozen samples in seriatim from said cryostat to a NMR probe of the nuclear magnetic spectrometer apparatus;
   heating each given sample while the given sample is disposed in the NMR probe; and
   immediately upon heating of each selected one of said samples, operating the nuclear magnetic spectrometer apparatus to obtain a spectrum from said selected one of said samples,
   wherein the moving of the frozen sample from said cryostat to said NMR probe includes shifting the samples in a first direction from said cryostat, in a second direction toward an axis of said probe, and in a third direction along said axis into said probe.

18. A method for gathering data using a nuclear magnetic spectrometer apparatus, comprising:
   subjecting a plurality of samples simultaneously cryogenic temperatures in a cryostat disposed within the nuclear magnetic spectrometer apparatus;
   moving the cryogenically frozen samples in seriatim from said cryostat to a NMR probe of the nuclear magnetic spectrometer apparatus;
   heating each given sample while the given sample is disposed in the NMR probe; and
   immediately upon heating of each selected one of said samples, operating the nuclear magnetic spectrometer apparatus to obtain a spectrum from said selected one of said samples,
   wherein the heating of each said given sample includes directing a laser beam along an axis of said probe to the given sample in the NMR probe.

\* \* \* \* \*